United States Patent
Boulis et al.

(10) Patent No.: US 10,866,291 B2
(45) Date of Patent: Dec. 15, 2020

(54) DEVICES AND SYSTEMS FOR MRI-GUIDED PROCEDURES

(71) Applicant: EMORY UNIVERSITY, Atlanta, GA (US)

(72) Inventors: Nicholas M. Boulis, Atlanta, GA (US); John N. Oshinski, Decatur, GA (US); Jason J. Lamanna, Atlanta, GA (US); Cody Dillion Anderson, Atlanta, GA (US)

(73) Assignee: Emory University, Atlanta, GA (US)

( * ) Notice: Subject to any disclaimer, the term of this patent is extended or adjusted under 35 U.S.C. 154(b) by 1144 days.

(21) Appl. No.: 14/851,524

(22) Filed: Sep. 11, 2015

(65) Prior Publication Data
US 2016/0074119 A1    Mar. 17, 2016

Related U.S. Application Data

(60) Provisional application No. 62/049,526, filed on Sep. 12, 2014.

(51) Int. Cl.
*G01R 33/28* (2006.01)
*A61B 50/20* (2016.01)
(Continued)

(52) U.S. Cl.
CPC ............ *G01R 33/285* (2013.01); *A61B 50/20* (2016.02); *A61B 90/11* (2016.02); *A61B 17/17* (2013.01);
(Continued)

(58) Field of Classification Search
CPC ....... A61B 90/11; A61B 90/10; A61B 90/101; A61B 2090/103; A61B 50/20; A61B 50/21; A61B 50/22; A61B 50/24; A61B 17/17; A61B 17/1735; A61B 17/1757; G01R 33/285; G01R 33/286; G01R 33/287

See application file for complete search history.

(56) References Cited

U.S. PATENT DOCUMENTS

| | | | |
|---|---|---|---|
| 6,132,437 A * | 10/2000 | Omurtag | A61B 90/11 600/417 |
| 6,546,277 B1 | 4/2003 | Franck et al. | |

(Continued)

FOREIGN PATENT DOCUMENTS

| | | |
|---|---|---|
| WO | 2000/007652 A1 | 2/2000 |
| WO | 2000/023000 A1 | 4/2000 |

*Primary Examiner* — Amanda Lauritzen Moher
*Assistant Examiner* — Chao Sheng
(74) *Attorney, Agent, or Firm* — Emory Patent Group

(57) ABSTRACT

Devices and systems can be configured to guide an instrument to a target region. The guide system may include an imaging guide including a first segment, the first segment including a guide region and imaging coils surrounding the guide region; and a platform. The platform may include a first rail, a second rail disposed parallel to the first rail, and a positioning member disposed between the first rail and the second rail. The positioning member may include a positioning frame having an entry region. The positioning frame may be movably disposed with respect to the first and second rails in a first direction and a second direction that is perpendicular to the first direction. The platform may be disposed with respect to the imaging guide so that a position of the entry region is within the guide region.

19 Claims, 8 Drawing Sheets

(51) Int. Cl.
*A61B 90/11* (2016.01)
*A61B 90/10* (2016.01)
*A61B 17/17* (2006.01)
*A61B 50/24* (2016.01)
*A61B 50/22* (2016.01)

(52) U.S. Cl.
CPC ....... *A61B 17/1735* (2013.01); *A61B 17/1757* (2013.01); *A61B 50/22* (2016.02); *A61B 50/24* (2016.02); *A61B 90/10* (2016.02); *A61B 2090/103* (2016.02); *G01R 33/286* (2013.01); *G01R 33/287* (2013.01)

(56) References Cited

U.S. PATENT DOCUMENTS

| | | | |
|---|---|---|---|
| 6,796,988 B2 | 9/2004 | Melkent et al. | |
| 2005/0216026 A1* | 9/2005 | Culbert | A61B 17/17 606/96 |
| 2008/0306375 A1* | 12/2008 | Sayler | A61B 5/055 600/417 |
| 2009/0088627 A1* | 4/2009 | Piferi | A61B 5/055 600/422 |
| 2010/0030184 A1* | 2/2010 | Boulis | A61B 17/0206 604/500 |
| 2011/0319745 A1* | 12/2011 | Frey | A61B 17/15 600/407 |
| 2014/0275978 A1* | 9/2014 | Fujimoto | G01R 33/287 600/422 |

\* cited by examiner

DEVICES AND SYSTEMS FOR MRI-GUIDED PROCEDURES

CROSS REFERENCE TO RELATED APPLICATION

This application claims priority to Provisional Application Ser. No. 62/049,526 filed on Sep. 12, 2014, which is hereby incorporated by reference in its entirety.

BACKGROUND

Both injury (trauma) and disease can damage the spine and lead to a wide host of symptoms including pain, weakness, paralysis and even incontinence. Regardless of the cause, damage to the spine, and more specifically, the spinal cord, is highly challenging to treat and currently met with a poor prognosis. Many promising avenues for treating the spinal cord are in development including small molecule therapies, biologics (protein-based therapeutics), functional electrical stimulation, and the application of stem cells. One of the key challenges in addressing these injuries or damage, regardless of the type, is an inability to effectively and accurately deliver therapies to the targets on and/or around the spinal cord. Currently, surgeons generally have to rely on preoperative imaging (MRIs) and intra-operative visual inspection of the cord to locate their targets to receive delivery of the treatment. Invasive surgery (e.g., multi-level laminectomy) is therefore generally required to provide intra-operative access to the spinal cord

SUMMARY

Thus, there is a need for a less-invasive, MRI compatible surgery platform.

This disclosure is directed to systems and devices that can help identify the targets to receive a therapy and that is capable of being used with real-time imaging. The systems and devices according to embodiments can therefore potentially reduce the invasiveness of delivering therapies to the spinal cord.

In some embodiments, the disclosure relates to a surgical guide system. In some embodiments, the guide system may include an imaging guide including a first segment. The first segment may include a guide region and imaging coils surrounding the guide region. In some embodiments, the guide system may include a platform that includes a first rail, a second rail disposed parallel to the first rail, and a positioning member disposed between the first rail and the second rail. The positioning member may include a positioning frame configured to mount an instrument The positioning frame may include an entry region and be movably disposed with respect to the first and second rails in a first direction and a second direction that is perpendicular to the first direction. In some embodiments, the platform may be disposed with respect to the imaging guide so that a position of the entry region is within the guide region.

In some embodiments, the disclosure relates to an imaging guide. The imaging guide may include a first segment, the first segment including a guide region and imaging coils surrounding the guide region. In some embodiments, the imaging coils may be radiofrequency coils.

Additional advantages of the disclosure will be set forth in part in the description which follows, and in part will be obvious from the description, or may be learned by practice of the disclosure. The advantages of the disclosure will be realized and attained by means of the elements and combinations particularly pointed out in the appended claims. It is to be understood that both the foregoing general description and the following detailed description are exemplary and explanatory only and are not restrictive of the disclosure, as claimed.

BRIEF DESCRIPTION OF THE DRAWINGS

The disclosure can be better understood with the reference to the following drawings and description. The components in the figures are not necessarily to scale, emphasis being placed upon illustrating the principles of the disclosure.

DESCRIPTION OF THE EMBODIMENTS

Figure 1:
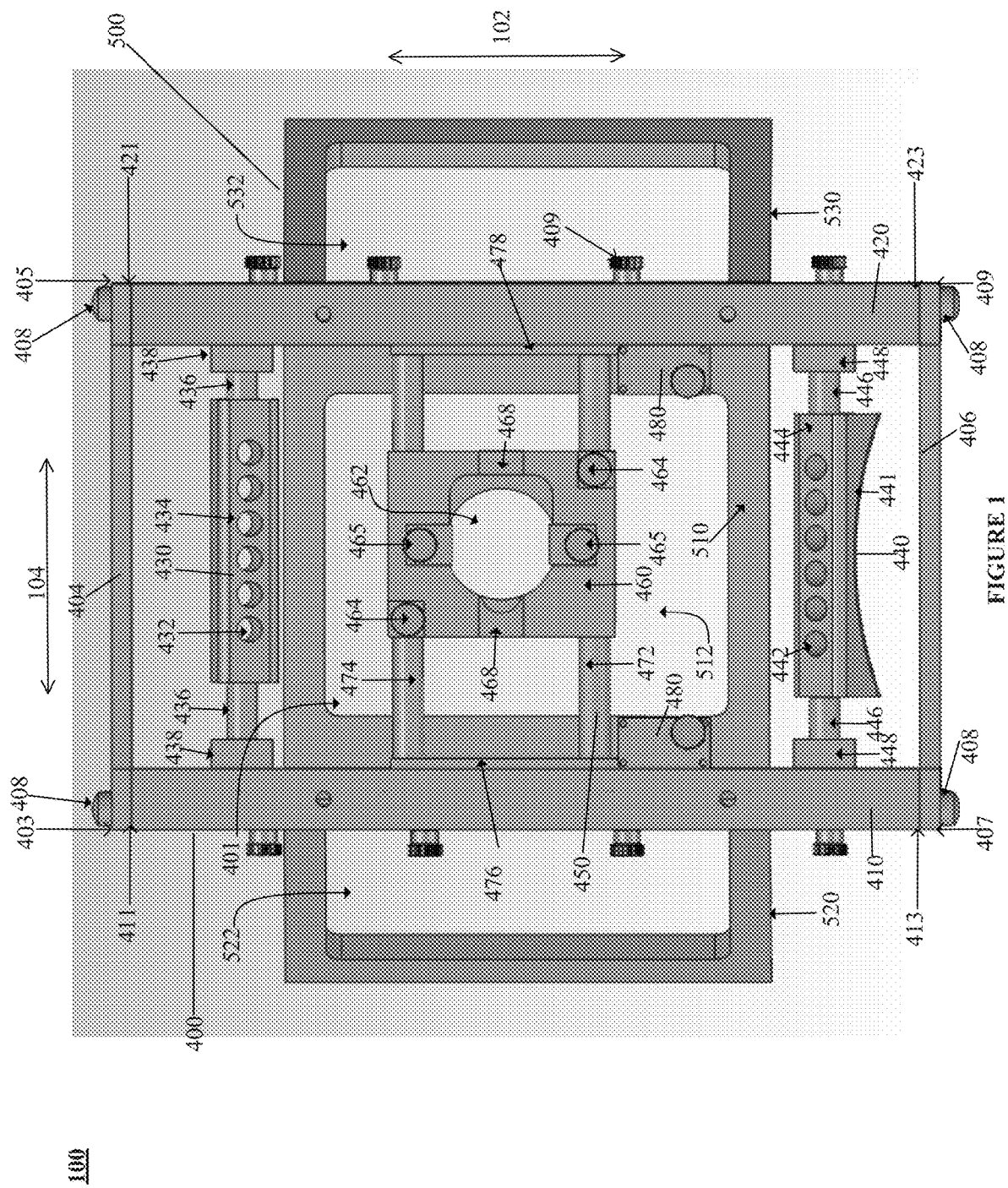
FIG. 1 shows a view of a system according to embodiments.

In the following description, numerous specific details are set forth, such as examples of specific components, devices, methods, etc., in order to provide a thorough understanding of embodiments of the disclosure. It will be apparent, however, to one skilled in the art that these specific details need not be employed to practice embodiments of the disclosure. In other instances, well-known materials or methods have not been described in detail in order to avoid unnecessarily obscuring embodiments of the disclosure. While the disclosure is susceptible to various modifications and alternative forms, specific embodiments thereof are shown by way of example in the drawings and will herein be described in detail. It should be understood, however, that there is no intent to limit the disclosure to the particular forms disclosed, but on the contrary, the disclosure is to cover all modifications, equivalents, and alternatives falling within the spirit and scope of the disclosure.

Unless otherwise defined, all terms (including technical and scientific terms) used herein have the same meaning as commonly understood by one of ordinary skill in the art to which this invention belongs. It will be further understood that terms, such as those defined in commonly used dictionaries, should be interpreted as having a meaning that is consistent with their meaning in the context of the specification and relevant art and should not be interpreted in an idealized or overly formal sense unless expressly so defined herein. Well-known functions or constructions may not be described in detail for brevity and/or clarity.

The term "MRI scanner" refers to a magnetic resonance imaging and/or NMR spectroscopy system. As is well known, MRI scanners include a low field strength magnet (typically between about 0.1 T to about 0.5 T), a medium field strength magnet, or a high-field strength super-conducting magnet, an RF pulse excitation system, and a gradient field system. MRI scanners are well known to those of skill in the art. Examples of commercially available clinical MRI scanners include, for example, those provided by General Electric Medical Systems, Siemens, Philips, Varian, Bruker, Marconi, Hitachi and Toshiba. The MRI systems can be any suitable magnetic field strength, such as, for example, about 1.5 T or about 3.0 T, and may include other high-magnetic field systems between about 2.0 T-10.0 T.

The term "MRI visible" means that the device is visible, directly or indirectly, in an MRI image. The visibility may be indicated by a change in SNR of the MRI signal proximate the device.

The term "MRI compatible" means that the so-called component(s) is suitable for use in an MRI environment and as such is typically made of a non-ferromagnetic MRI compatible material(s) suitable to reside and/or operate in or proximate a conventional medical high magnetic field environment. The "MRI compatible" component or device is "MR safe" when used in the MRI environment and has been demonstrated to neither significantly affect the quality of the diagnostic information nor have its operations affected by the MR system at the intended use position in an MR system. These components or devices can generally meet the standards defined by ASTM F2503-05. See, American Society for Testing and Materials (ASTM) International, Designation: F2503-05. Standard Practice for Marking Medical Devices and Other Items for Safety in the Magnetic Resonance Environment. ASTM International, West Conshohocken, Pa., 2005. Exemplary MRI-compatible (non-ferromagnetic) materials include, but are not limited to, various polymeric materials (e.g., plastics), carbon fiber materials, glass-filled epoxies, and metals such as nickel-titanium alloys (e.g., Nitinol).

The term "imaging coils" refers to a device that is configured to operate as an MRI receive antenna, such as radiofrequency coils. The term "coil" with respect to imaging coils is not limited to a coil shape but is used generically to refer to any MRI antenna configurations, loopless, looped, etc., as are known to those of skill in the art.

The disclosures relate to devices and systems for guiding an instrument to a target region. The devices and systems according to the disclosure can be configured to guide any medical instrument with respect to internal and/or external regions of the body of a patient. An instrument may be any medical device (e.g., diagnostic devices, interventional devices, etc.) configured to deliver a therapy to a target region. The therapy may include but is not limited to injections, biopsy, fusion, injections of therapeutics (e.g., stem cells, biologicals, small molecule therapies, protein-based therapies, etc.), or stimulation. In some embodiments, the devices and systems may be used to position an instrument to deliver a therapy to a target in and around the spine. In other embodiments, the devices and systems may be used to position an instrument to deliver a therapy to another target region.

In some embodiments, the devices and systems may include a platform configured to securely position an instrument for delivering a therapy to a target region and an imaging guide configured to provide visualization of the target region. The devices and systems can be MRI compatible. The devices and systems may also be sized so as to be capable of fitting within a bore of an MRI scanner when provided on a patient. The devices and system can be used with any MRI scanner system, including open and closed bore designs and any field strength. For example, the field strength can be about 1.5 T or about 3.0 T, and can include other high-magnetic field systems between about 2.0 T-10.0 T (e.g., about 7.0 T). The devices and systems can be used to deliver a therapy to a target region under MRI guidance. In this way, the devices and systems can provide direct visualization of the underlying anatomy and/or the target regions and thereby provide a guide for a more accurate and safe delivery of therapies.

The devices and systems according to embodiments can thus overcome the conventional methods and devices for directly targeting specific anatomic structures, for example, within the spinal cord, that rely on preoperative MRI and naked-eye visual inspection of spinal cord surface anatomy. Additionally, the devices and systems according to embodiments can eliminate the need of certain invasive surgical procedures (e.g., laminectomy) that generally have been necessary to provide intra-operative access to target region(s) in the spinal cord and/or spine.

Figure 2:
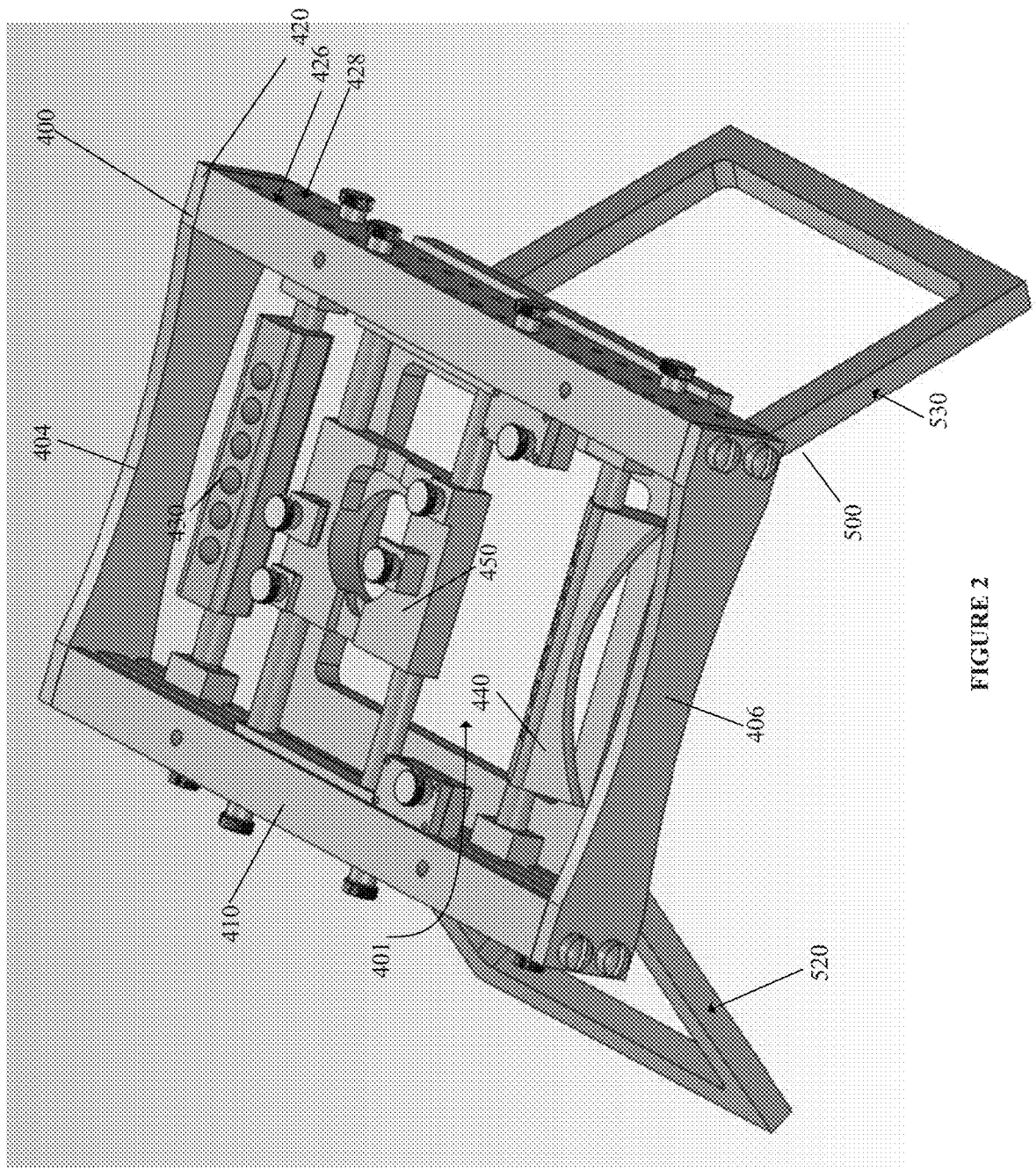
FIGS. 2 and 3 show other views of the system shown in FIG. 1 according to embodiments.
Figure 3:
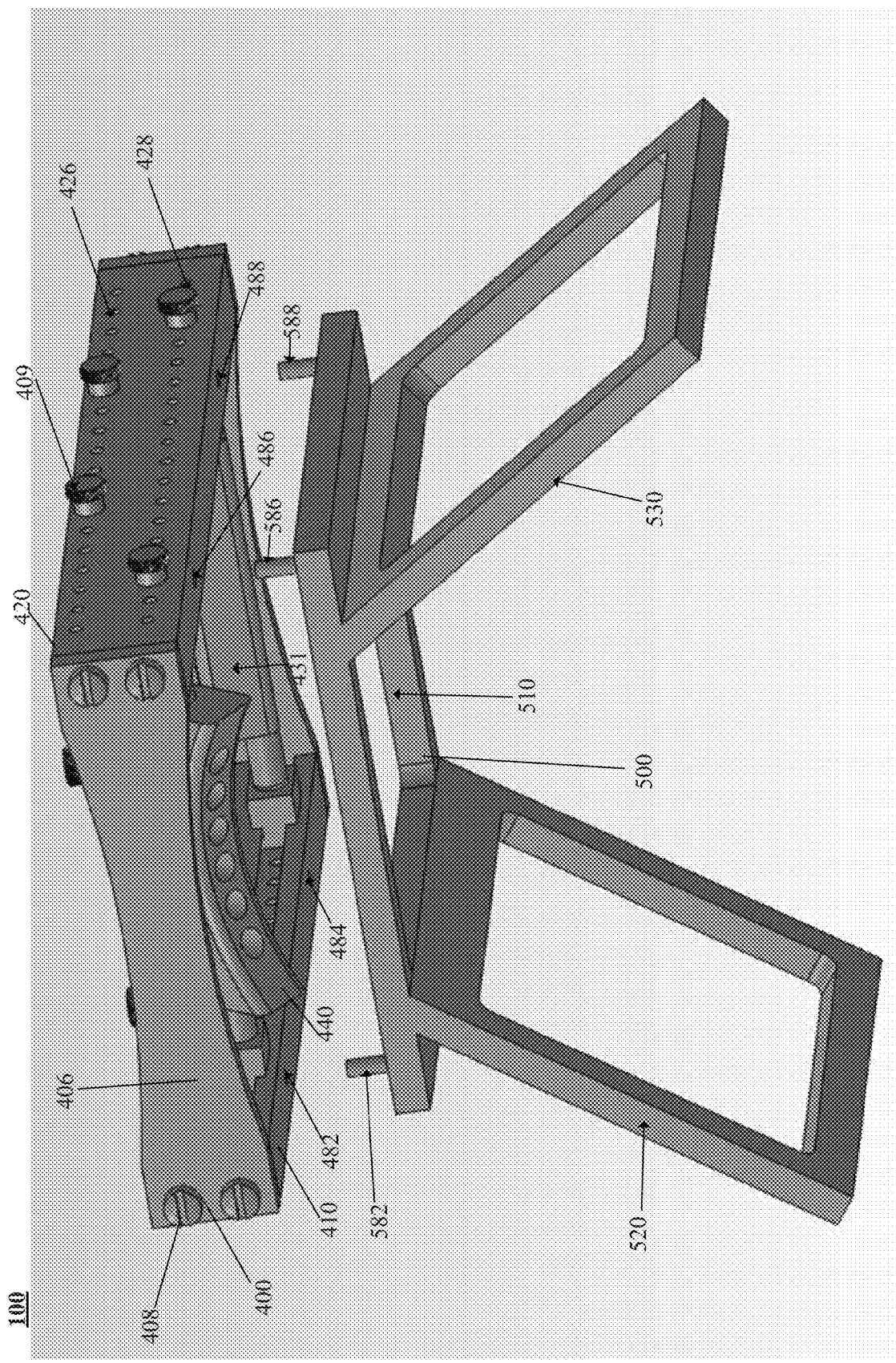

FIGS. 1-8 shows a surgical guide system 100 according to embodiments. In some embodiments, the guide system 100 may include a platform 400 and an imaging guide 500, as shown in FIGS. 1-3. It will also be understood that the guide system is not limited to the configuration and/or combination of the platform and the imaging guide shown in the figures. For example, the imaging guide 500 may be disposed below the platform 400 in some embodiments, as shown in FIGS. 1-3. In other embodiments, the imaging guide 500 may be disposed above the platform 400. For example, the imaging guide 500 may be disposed with respect to the platform 400 so as to not to interfere with an instrument mounted on the platform 400. In some embodiments, the guide system 100 may include a different platform and/or imaging guide. In some embodiments, the platform 400 and the imaging guide 500 may be used separately and/or may be respectively used with a different imaging guide or platform.

Figure 4:
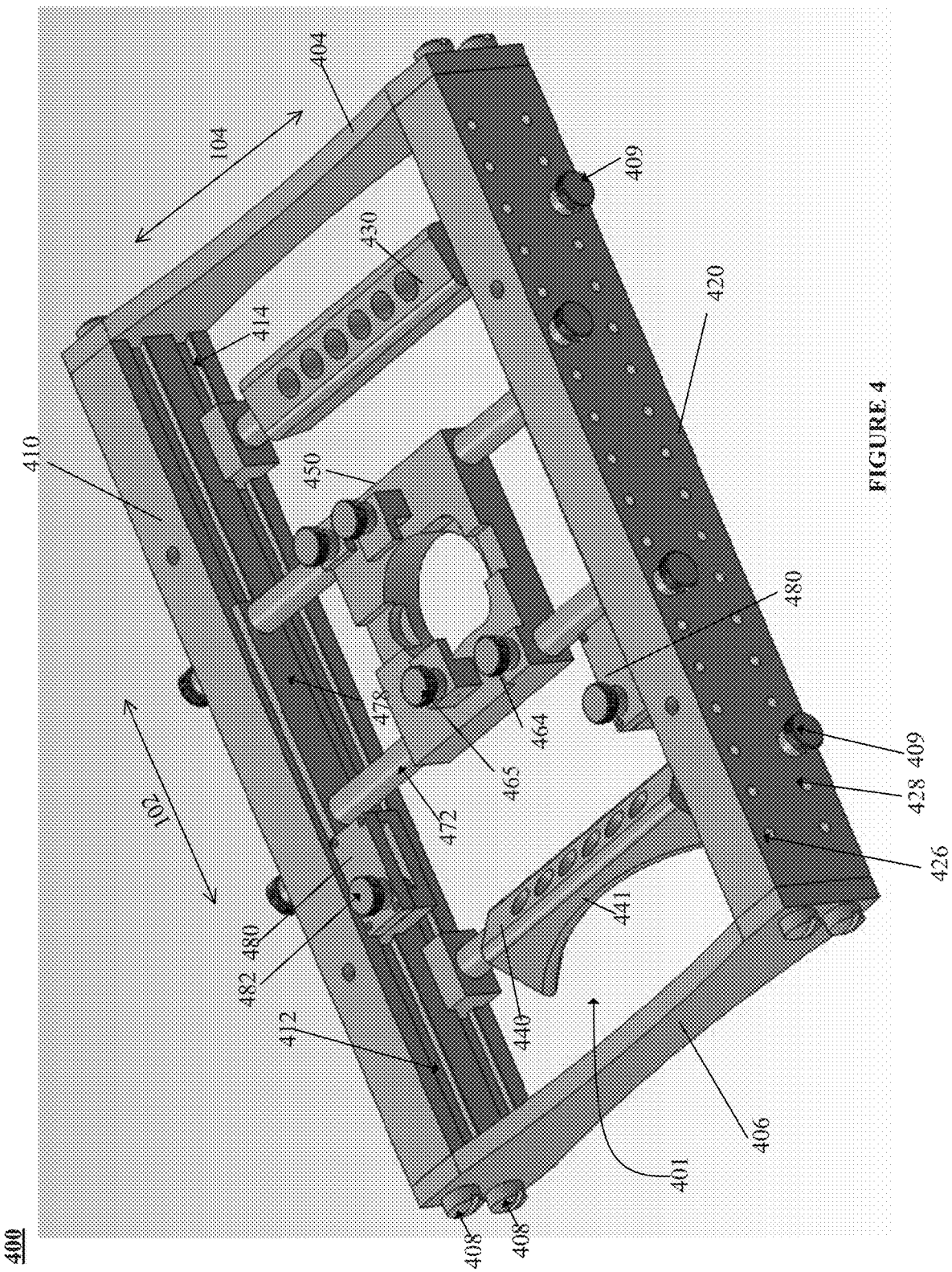
FIG. 4 shows the platform shown in FIGS. 1-3 according to embodiments.
Figure 5:
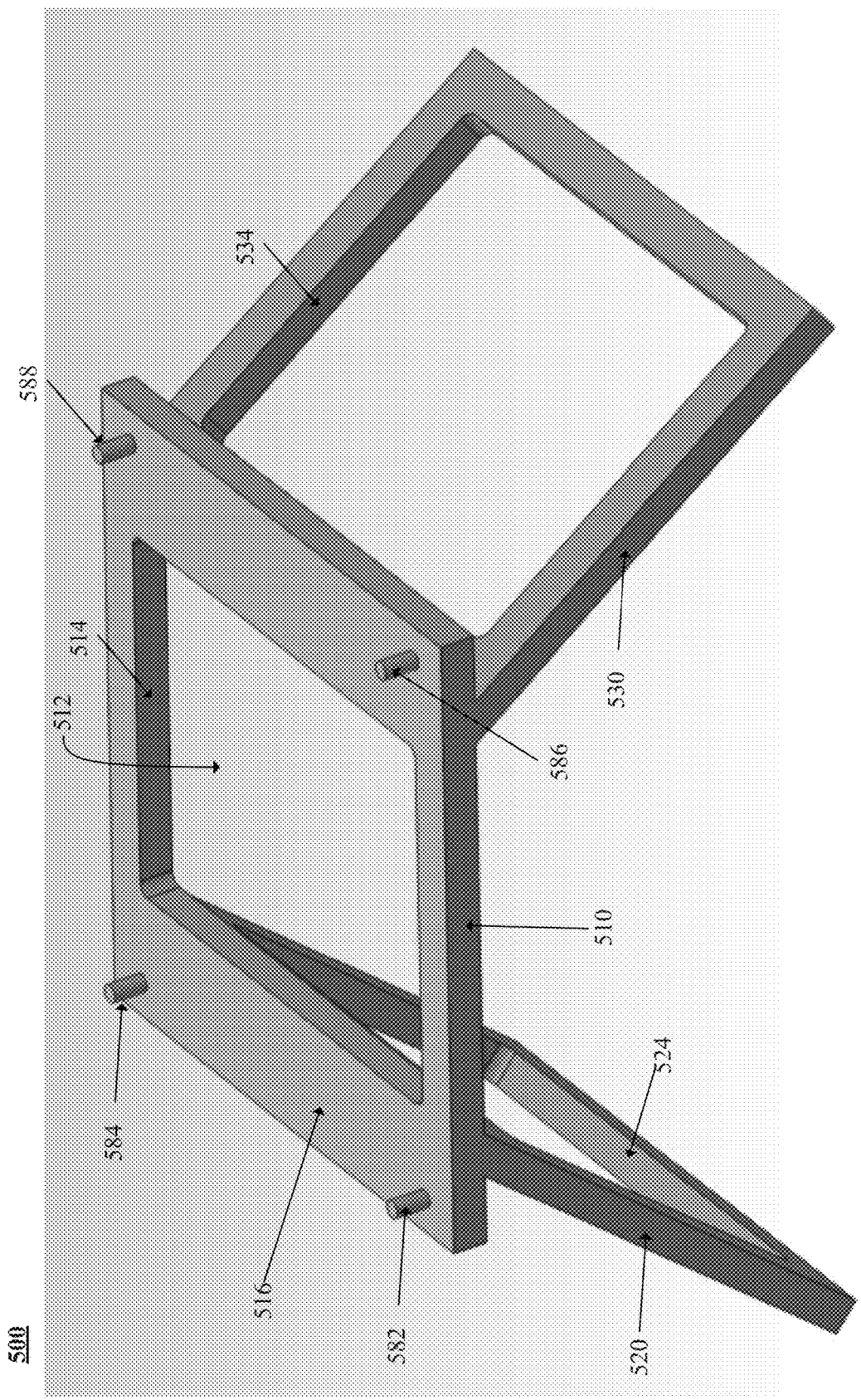
FIG. 5 shows the imaging guide shown in FIGS. 1-3 according to embodiments.
Figure 7:
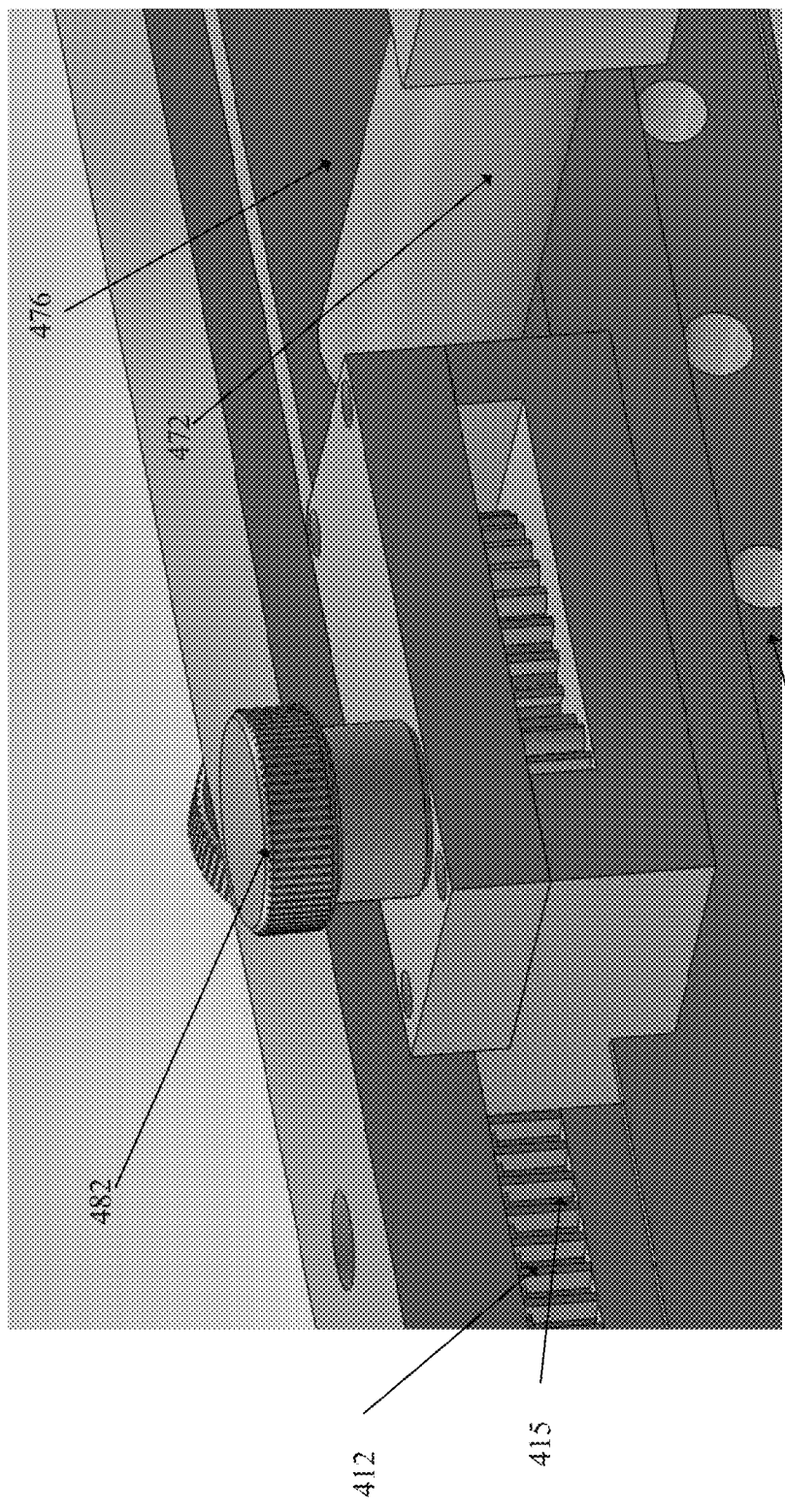
FIG. 7 shows a partial enlarged view of the platform shown in FIG. 4 according to embodiments.
Figure 8:
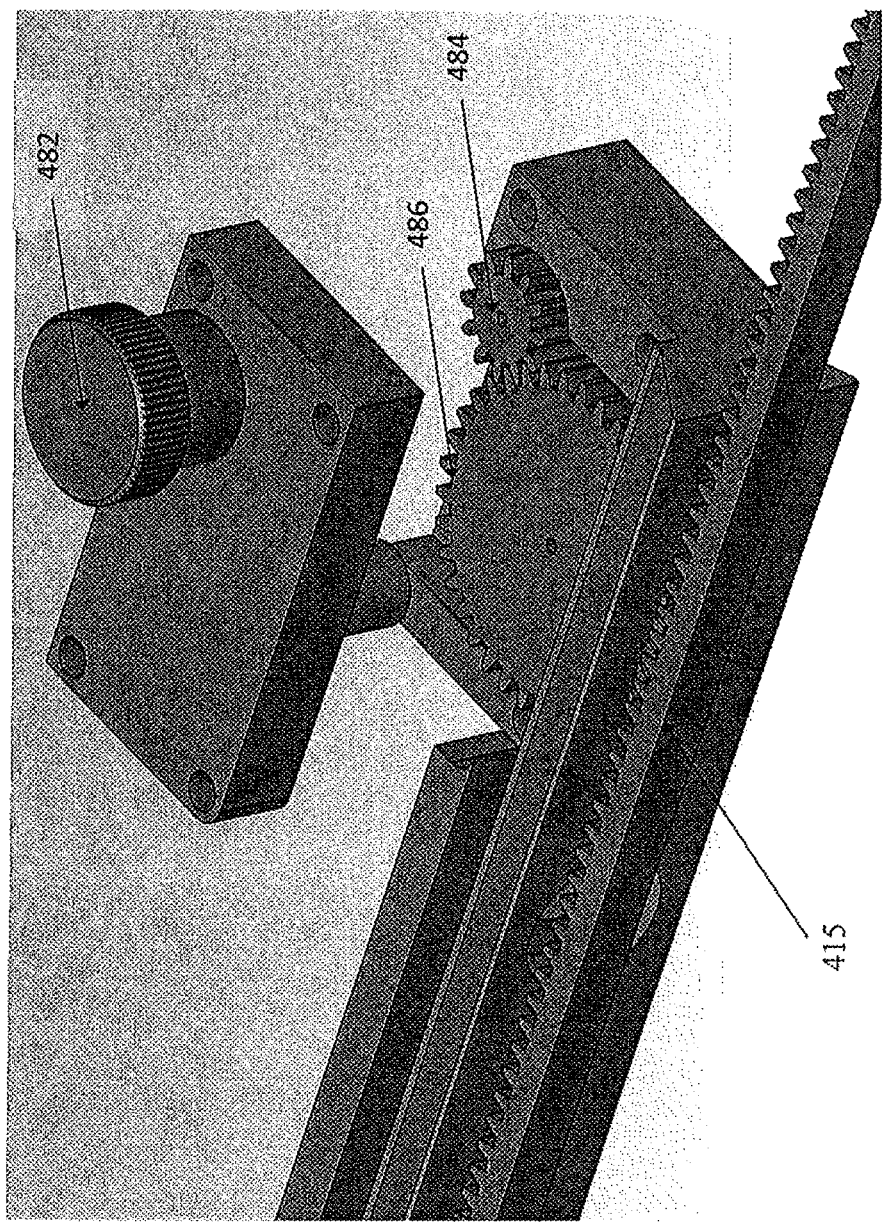
FIG. 8 shows a partial exploded view of the platform shown in FIG. 7.

In some embodiments, the platform 400 may be configured to provide a guide and stabilize an instrument with respect to a target region of a patient. FIGS. 4, 7 and 8 show the platform 400 shown in FIGS. 1-3 without an imaging guide.

In some embodiments, the platform 400 may include a positioning member 450 configured to position an instrument with respect to a target region. In this way, the platform 400 can provide stabilized movement for an instrument mounted on the positioning member 450 in the x (medial/lateral) and y (proximal/distal (e.g., caudal/rostral)) planes, while guiding the instrument to the target region under MRI guidance.

As shown in FIGS. 1-4, the platform 400 may include a first member rail 410 and a second rail member 420. The first rail member 410 and the second rail member 420 may be disposed in parallel to each other, for example, in plane 102. In some embodiments, the first rail member 410 may have a first end 411, a second end 413, and a length there between; and the second rail member 420 may have a first end 421, a second end 423, and a length there between. The length of the first rail member 410 and the length second rail member 420 may be any length. In some embodiments, the length of the first rail member 410 and the second rail member 420 may be the same.

In some embodiments, the platform 400 may include one or more support members configured to support the platform 400 with respect to a target region (e.g., head/neck/spine). In some embodiments, the one or more support members may be configured to temporarily fixate to the target region. In some embodiments, the platform 400 may include a first support member 430 and a second support member 440. In some embodiments, the first support member 430 and the second support member 440 may have a length that extends in a plane 104 that is perpendicular to the plane 102.

In some embodiments, the first support member 430 and the second support member 440 may be disposed in parallel to each other, for example, in the plane 104. In some embodiments, the first support member support member 430 and the second support member 440 may extend between and be perpendicular to the first rail member 410 and the second rail member 420. In some embodiments, the first rail member 410 and the second rail member 420 may be separated by the first support member 430 and the second support member 440.

In some embodiments, the platform 400 may include members 404 and 406 disposed at opposing ends of the first rail member 410 and the second rail member 420. The members 404 and 406 may be disposed so as to be parallel to the first and second support members 430 and 440. In some embodiments, the members 404 and 406 may be fixedly disposed to the ends of the first rail member 410 and the second rail member 420, for example, by one or more fasteners 408. In some embodiments, the one or more fasteners 408 may be screws. In some embodiments, the member 404 may have a first end 403, a second end 405, and a length there between; and the member 406 may have a first end 407, a second end 409, and a length there between. The length of the members 404 and 406 may be any length. In some embodiments, the length of the members 406 and 404 may be the same. In some embodiments, the length of the members 406 and 404 may include the length of separation between the first rail member 410 and the second rail member 420.

In some embodiments, the members 404 and 406 may include curved surface along the length on one or both sides. In some embodiments, the members 404 and 406 may also have a curved surface on the opposing side. In some embodiments, the surface(s) of the members 404 and 406 may have a different shape and/or different contour, for example, a substantially even surface along the length.

In some embodiments, the member 404 and/or the member 406 may be omitted. In this example, the first support member 430 and the second support member 440 may be disposed adjacent to the opposing ends of the first rail 410 and the second rail 420.

In some embodiments, the first rail member 410 and the second rail member 420 may each include one or more tracks disposed substantially along the length of the respective rail member. Each track may be configured to allow the positioning member 450 and/or support members 430 and/or 440 to move in either direction along the plane 102. As shown in FIGS. 1-4, the first rail member 410 and the second rail member 420 may respectively include two tracks. In other embodiments, the first rail member 410 and the second rail member 420 may include more or less tracks. In some embodiments, the first rail member 410 may include a first track 412 and a second track 414 and the second rail member 420 may include a first track 422 and a second track 424 (not visible due to orientation of the platform 400 in the drawings).

In some embodiments, the tracks 412, 422, 414 and 424 may be the same, different, or a combination thereof. For example, the tracks 412 and 422 may be different from the tracks 414 and 424. By way of another example, the tracks 412 and 422 and/or the tracks 414 and 424 may be different from each other, such as, different depths, different lengths, different heights, among others, or a combination thereof.

In some embodiments, the first track 412 of the first rail member 410 and the first track 422 of the second rail member 420 may be disposed above the second track 414 of the first rail member 410 and the second track 424 of the second rail member 420, respectively. In some embodiments, the first tracks 412 and 422 may be disposed at the same heights on the respective trail member and the second tracks 414 and 424 may be disposed at the same heights on the respective trail member. In some embodiments, the tracks 412, 422, 414 and/or 424 may have the same length, different lengths, or a combination thereof. For example, as shown in the figures, the tracks 412, 422, 414, and 424 are shown to have substantially the same length. The length of the tracks 412, 422, 414, and 424 substantially correspond to the length of the first rail member 410 and the second rail member 420. By way of example, in some embodiments, the tracks 412 and 414 may have a different length than the tracks 414 and 424, respectively.

In some embodiments, the first support member 430 and the second support member 440 may be disposed on the second tracks 414 and 424 and the positioning member 450 may be disposed on the first tracks 412 and 422. In this way, the positioning member 450 may be positioned along the length of the rail members 410 and 420 without interfering with the movement of the first support member 430 and the second support member 440 along the length of the rail members 410 and 420. Additionally, by providing the positioning member 450 higher than the support members 430 and 440, unrestricted access to the device attached to the positioning member 450 can be provided.

In some embodiments, one or more of the tracks 412, 414, 422, and 424 may include a cavity or recess configured to receive a portion of the positioning device 450 and/or the support members 430 and/or 440. In some embodiments, the recesses may include a smooth surface and/or the textured surface. For example, as shown in the FIGS. 1-4, 7 and 8, the tracks 412 and 422 may include a geared teeth surface 415 and 425, respectively (geared teeth surface 415 not visible due to orientation of the platform 400 in the drawings). In some embodiments, the geared teeth surface 415 and 425 may be disposed within a recessed track 412 and 422 so as to be flush with the inner surface of the members 410 and 420, respectively. In other embodiments, the tracks 412 and 422 may be of a different shape and/or configuration.

In some embodiments, the first rail member 410 and the second rail member 420 may include one or more rows of positioning guides. In some embodiments, the number of rows of positioning guides may depend on the number of tracks. In some embodiments, as shown in the figures, the first rail member 410 may include a first row of positioning guides 416 and a second row of positioning guides 418, which corresponds to the first track 412 and the second track 414, respectively (rows 416 and 418 not visible due to orientation of the platform 400 in the drawings); and the second rail member 420 may include a first row of positioning guides 426 and a second row of positioning guides 428, which corresponds to the first track 422 track and the second track 424, respectively. In other embodiments, the rail members 410 and 420 may include more or less rows. In some embodiments, the row of the positioning guides 416 and 426 may be disposed above the teeth surface 415 and 425, respectively.

In some embodiments, each row of positioning guides may be disposed substantially along the length of the rail members 410 and 420 corresponding to the location of the respective tracks. In some embodiments, each row of positioning guides may be disposed on a side (e.g., outer surface) of the rail members 410 and 420, respectively, that opposes the side (e.g., inner surface) in which the respective tracks are disposed.

In some embodiments, each positioning guide may be configured to fix the position of the positioning member 450 and/or the first support member 430 and/or the second support member 440 with respect to the first rail member 410 and the second rail member 420. In some embodiments, each positioning guide may be a hole. In some embodiments, the hole may extend from the outer surface to the inner surface of each respective rail member. Each positioning guide may be a hole configured to receive one or more fasteners 409 configured to fix the positioning member 450 and/or the first support member 430 and/or the second support member 440 with respect to the first rail member 410 and the second rail member 420, respectively. In some embodiments, the one or more fasteners 409 may be any fastener, including but not limited to screw (e.g., as shown in the figures), pins, bolts, among others, or a combination thereof.

The positioning guides and/or rows are not limited to the size, shape, number, spacing, pattern, depth, etc. of the holes shown in the figures. The positioning guides and/or rows may include holes of any shape, size, number, spacing, pattern, depth, etc. The shape, size, depth, etc., of the positioning guides may be modified to correspond to the dimensions of the fasteners to be used. In some embodiments, the system 100 may include one or more fasteners. For example, in some embodiments, the system 100 may include fasteners 409 configured to removably fasten the positioning member 450 and/or the first support member 430 and/or the second support member 440 with respect to the (length of the) first rail member 410 and the second rail member 420 via a positioning guide (hole) disposed in the tracks, for example, by tensioning against a back surface (surface facing the track) of the respective member. In other embodiments, the positioning guides are also not limited holes and may have a different shape and/or configuration.

In this way, the positioning member 450 and/or the first support member 430 and/or the second support member 440 may be stabilized in a direction along the plane 102. Additionally, the fixed position of the positioning member 450 and/or the first support member 430 and/or the second support member 440 with respect to the plane 102 can be easily adjusted. For example, the fasteners 409 may be removed and 1) the positioning member may be moved along the tracks 412 and 422 to a different position and fixed at the position by utilizing fasteners in the positioning guides 416 and 426; and/or 2) the first support member 430 and/or the second support member 440 may be moved along the tracks 414 and 424 to a different position and fixed at the position by utilizing fasteners in the positioning guides 418 and 428.

In some embodiments, the positioning guides may be configured to be used as markers during a MRI guided procedure system. For example, the MRI guided procedure system may provide guidance of the position of the instrument mounted on the positioning member 450 in the plane 102 with respect to the positioning guides.

In some embodiments, the first support member 430 and the second support member 440 may include a plurality of fixating members 432 and 442, respectively, disposed along a portion of their length. The fixating members 432 and 442 may be holes configured to receive one or more fasteners (e.g., screws) (fasteners not shown), for example, to attach or fixate the platform to a region of the patient. The members 432 and 442 are not limited to the size, shape, number, spacing, pattern, depth, etc. of the holes shown in the figures. The members 432 and 442 may be holes of any shape, size, number, spacing, pattern, depth, etc. The shape, size, depth, etc., of the members 432 and 442 may be modified to correspond to the dimensions of the fasteners to be used. In some embodiments, the system 100 may include fasteners configured for members 432 and 442.

In some embodiments, the fixating members 432 and 442 may be disposed on portions 434 and 444, respectively, of the support members 430 and 440. In some embodiments, the members 432 and 442 may be configured to fixate the platform 400 to a region of patient, for example, using fasteners (e.g., screws). By way of example, the platform 400 may be fixated to a spine of the patient by spinal screws provided in the one or more members 432 and 442. In some embodiments, the system 100 may include the fasteners.

In some embodiments, the portions 434 and the 444 may have any shape. In some embodiments, the surfaces of the respective portions 434 and 444 may have the same shape, different shape, or a combination thereof. In some embodiments, the portions 434 and 444 may include flat, contoured or curved surfaces, among others, or a combination thereof on one or more sides. In some embodiments, the portion 434 may include a flat surface 431 and the portion 444 may include a curved or contoured surface on a side through which the members 432 and 442 are disposed. The curved or contoured surface 441 may be configured to be disposed on the target region. With respect to member 430, either side of the member 430 through which the members 432 are disposed may be disposed on the target region because the surface 431 is flat. For example, the surface 431 and 441 may better positioned and fixate the platform 400 to the target region. In some embodiments, the surfaces 431 and 441, as well as other surfaces of the portions 434 and 444, respectively, may have a different shape and/or different contour.

In some embodiments, the first support member 430 and the second support member 440 may be configured to individually rotate with respect to the first rail member 410 and the second rail member 420 in either direction. In this way, the first support member 430 and the second support member 440 can each be configured to linearly move and rotate with respect the first rail member 410 and the second rail member 420. This can allow a position of the first support member 430 and the second support member 440 to be individually adjusted with respect to a target region of the patient before the platform 400 is attached to a patient with fasteners. In some embodiments, the first support member 430 and the second support member 440 may each include one or more portions configured to facilitate the rotation of the respective members, for example, by a practitioner. In this way, the platform 400 can be easily tailored to different target regions, patient anatomy, fasteners, etc. that may arise during a delivery of a therapy.

In some embodiments, the one or more portions configured to facilitate the rotation of the respective members may be circular and may have a different diameter or width than the portions 434 and 444. As shown in the figures, the first support member 430 may include one or more portions 436 and the second support member 440 may include one or more portions 446. In some embodiments, the first support member 430 and the second support member 440 may each include two portions 436 and 446 disposed on either side of the portions 434 and 444 (with respect to the length of the respective support members), respectively, as shown in the figures. In other embodiments, the first support member 430 and the second support member 440 may include a different number and position of the portions 436 and 446. For example, the first support member 430 and/or the second support member 440 may include one portion 436 and/or 446 disposed on one side of the portions 434 and 444.

In some embodiments, the first support member 430 and the second support member 440 may each include a member 438 and a member 448, respectively, disposed on each end of the respective support member and configured to move the respective member along a track of the rail members 410 and 420. The members 438 and 448 may be configured to receive one or more fasteners 409 so that the first support member 430 and the second support member 440 can be adjustably fixedly dispose with respect to a corresponding number of position guides disposed on the rail members 410 and 420. In some embodiments, one or more fasteners 409 may be configured to tension against the back surface of the members 438 and 448 (the surface against the tracks 412 and 424 respectively) through a position guide, for example, disposed in rows 418 and 428, to more securely dispose the support members with respect to the rail members. In some embodiments, the back surface of the members 438 and 448 may have a shape complimentary to the tracks 412 and 424. In other embodiments, the fastening members 438 and 448 may have a different shape.

In some embodiments, the platform 400 includes a procedure region 401. The procedure region 401 may be considered a region defined by the first support member 430, the second support member 440, the first rail 410, and the second rail 420.

In some embodiments, the positioning member 450 may be configured to position and guide an instrument with respect to a target region of a patient. In some embodiments, the positioning member 450 may be configured to move in either direction in the plane 102 and the plane 104 within the procedure region 401.

In some embodiments, the positioning member 450 may include a positioning frame 460 configured to receive an instrument. It will be understood that the shape and/or configuration shown in the figures is merely an example for a specific type of instrument. The shape and/or configuration of the positioning frame 460 shown in the figures can be modified according to parameters (e.g., size, delivery mechanisms, sensors, etc.) to the instrument to be attached, for example, so that the instrument securely attaches to the frame 460.

In some embodiments, the positioning frame 460 may include an entry region 462 in which an instrument mounted on the positioning frame 460 may access a target region of a patient. The entry region 462 may be an opening disposed within the positioning frame 460. As shown in the figures, the entry region 462 may have a circular shape in some embodiments. The entry region 462 may have any shape, size, etc. For example, the entry region 462 may be modified according to parameters (e.g., size, delivery mechanism(s), sensors etc.) of the instrument to be mounted.

In some embodiments, the positioning frame 460 may include one or more fastening members 465 configured to fixedly dispose an instrument mounted to the frame 460. The one or more fastening members may depend on the parameters of the instrument to be mounted. In some embodiments, the one or more fastening members 464 may be configured to receive one or more fasteners configured to fixedly dispose an instrument to the frame 460. In some embodiments, the system 100 may include fasteners configured for the fastening members 465, as shown. The fasteners may include are not limited to thumb screw (as shown), bolts, pins, among others, or a combination thereof.

In some embodiments, the positioning frame 460 may include indentations 468 that may be complimentary to a specific instrument. Again, it will be understood that the fastening member(s) and the surfaces of the frame 460 on which they are disposed can be modified according to parameters (e.g., size, delivery mechanisms, sensors, etc.) to the instrument to be attached.

In some embodiments, the positioning member 450 may include a first elongated member 472 and a second elongated member 474 that are parallel to the support members 430 and 440. The first elongated member 472 and the second elongated member 474 may have a length extending between the first rail 410 and the second rail 420. The length of the elongated members 472 and 474 may be substantially similar to the length of the support members 430 and 440.

In some embodiments, the elongated members 472 and 474 may be separated by a fixed distance. The fixed distance may depend on the parameters of the instruments. In some embodiments, each end of the elongated members 472 and 474 may be fixed to a side of a first base member 476 and a second base member 478. The base members 476 and 478 may be configured to move along one of the tracks. For example, as shown in the figures, the base members 476 and 478 may be configured to move along the tracks 412 and 22. The other side (i.e., the back surface) of the base members 476 and 478 may have a shape complimentary to the tracks 412 and 422. In the figures, the base members 476 and 478 have a T-like shape that corresponds to the recess shape of the tracks 412 and 422.

The base members 476 and 478 may be each configured to receive one or more fasteners 409 so that the positioning member 450 can be adjustably fixedly dispose with respect to corresponding number of position guides disposed on the rail members 410 and 420. In some embodiments, one or more fasteners 409 may be configured to tension against the back surface of the members 438 and 448 (the surface against the tracks 412 and 424 respectively) through a position guide to more securely dispose the support members with respect to the rail members. As shown in the figures, the platform 400 includes two fasteners 409 to fixedly dispose each base member 476 and 478. In some embodiments, more or less fasteners 409 may be used to fixedly dispose the positioning member 450 via the base members 476 and 478 with respect to the members. For example, one fastener 409 may be used for each side. Additionally, other parts of the positioning member 450 may be used to fixedly dispose it with respect to the rail members (e.g., the movement mechanisms 480). In use, for example, a position of the positioning member 450 may be temporarily fixed with respect to the first rail member 410 and the second rail member 420 by inserting a fastener 409 in each opening of the base member via the positioning guide in rows 416 and 426 and tighten accordingly so there are two fasteners 409 disposed within each base member.

The positioning frame 460 can be configured to move along the elongated members 472 and 474 in either direction along the plane 104. In some embodiments, the positioning frame 460 may include one or more positioning guides 464 configured to fix the position of the positioning frame 460 with respect to the elongated members 472 and 474. In some embodiments, at least one member 464 may be disposed on each side of the positioning frame 460 above the respective elongated member 472 and 474. The guides 464 may be holes configured to receive one or more fasteners configured to fix the positioning frame 460 with respect to the elongated members 472 and 474, respectively. The guides 464 are not limited to the size, shape, number, spacing, pattern, depth, etc. of the holes shown in the figures. The guides 464 may be of any shape, size, number, spacing, pattern, depth, etc.

The shape, size, depth, etc., of the members 464 may be modified to correspond to the dimensions of the fasteners to be used. In some embodiments, the system 100 may include fasteners configured for the guides 464, as shown. The fasteners may include are not limited to thumb screw (as shown), bolts, pins, among others, or a combination thereof.

In some embodiments, the positioning member 450 may include one or more movement mechanisms 480 disposed directly adjacent to an elongated member (472 or 474) and respective base member. The one or more movement mechanisms may be configured to controllably move the positioning member 450 along the tracks 412 and/or 422 of the rail members 410 and 420, respectively. In some embodiments, the positioning member 450 may include a movement mechanism 480 disposed adjacent to the opposing ends of an elongated member. In other embodiment, the positioning member 450 may include more or less movement mechanisms 480.

The movement mechanism 480 may be complimentary to the surface of the track. For example, as shown, the tracks 412 and 422 may include a teeth surface 415 and 425. In some embodiments, the movement mechanism 480 may include a geared system configured to controllably move the positioning member 450 along the teethed surface.

For example, as shown in the partial enlarged view shown in FIG. 7 and a partial exploded view shown in FIG. 8 (with a portion of the rail member removed), the movement mechanism 480 may include a movement member 482 configured to cause the positioning member 450 to move along the tracks 412 and/or 422. In some embodiments, the movement member 482 may be a rotational member, such as a thumbnail screw (as shown), among others, or a combination thereof.

In some embodiments, the movement mechanism 480 may include one or more gears configured to translate the movement of the movement member 482 to linear movement along the tracks. As shown in the drawings, the movement mechanism 480 may include a gear 484 that is configured to communicate with a movement member 482 and translate that rotational movement to a gear 486 that is configured to translate that rotational movement to linear movement along the respective track, for example, by communicating with the respective teethed surface. In some embodiments, the movement member 482 may be disposed above gear 484. In some embodiments, the gear 486 may be larger than the gear 484. In some embodiments, the movement mechanism may include more gears, different gears (e.g., shape), among others, or a combination thereof.

In operation, an instrument mounted to the positioning frame 460 can be moved in the procedure region 401 in either direction along the planes 102 and 104. By way of example, the positioning frame 460 can be moved in either direction in the procedure region 401 in the plane 104 by moving the positioning frame along plane 104 along the length of the elongated members 472 and 474. The position frame 460 can be moved in either direction in the procedure region 401 in the plane 102 by moving the positioning member 450 along the tracks 412 and 422 of the rail members 410 and 420, respectively.

It is understood that for those features described but not clearly visible in the drawings due to the orientation of the platform in the drawings are identical to the corresponding features that may be more clearly visible, unless otherwise noted. For example, as shown in the drawings, the features of the first rail member 410 and the second rail 420 (e.g., the tracks) can be considered to be identical and therefore those features visible for one can be considered to be the same for the other.

Figure 6:
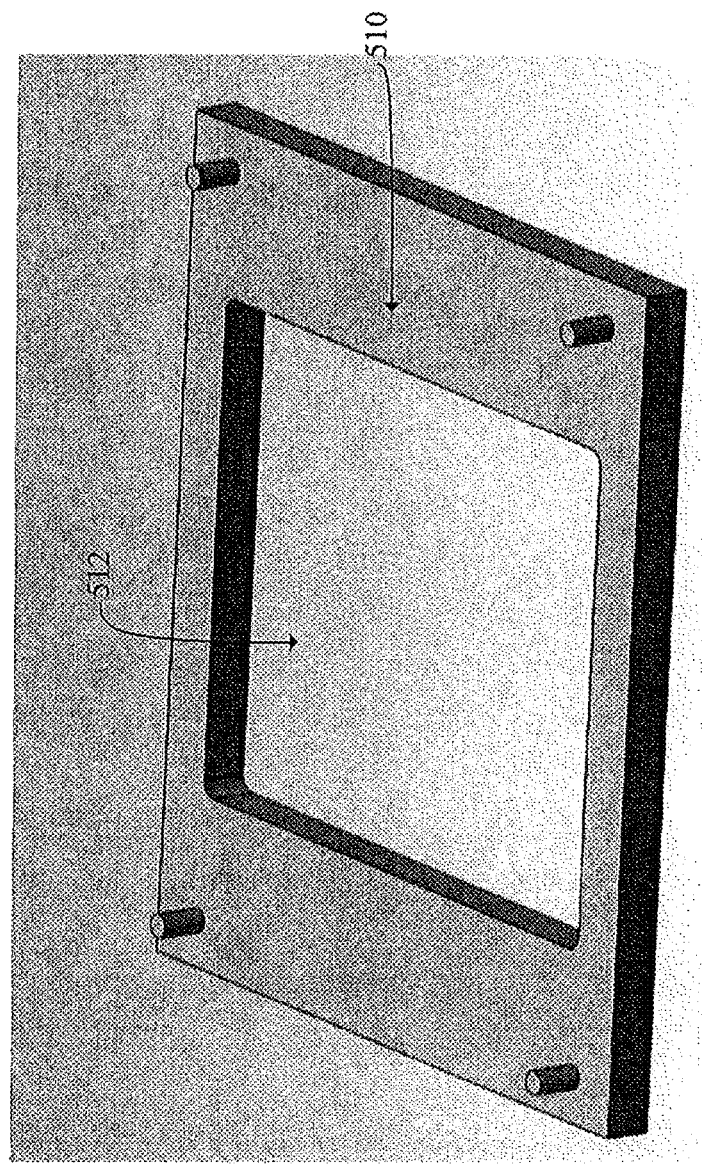
FIG. 6 shows the imaging guide according to embodiments.

FIGS. 1-3, 5 and 6 show the imaging guide 500 according to embodiments. As shown in the figures, the imaging guide 500 may include one or more segments. In some embodiments, the imaging guide 500 may include one segment (e.g., main segment) 510, for example, as shown in FIG. 6. In other embodiments, the imaging guide 500 may include more than one segment, for example, as shown in FIGS. 1-3 and 5. As shown in these figures, the imaging guide 500 may include additional segments 520 and 530 that extend from the main segment 510.

The one or more segments may have any shape. In some embodiments, the one or more segments may have a rectangular shape as shown in the figures. In other embodiments, the one or more segments may have a different shape. In the figures, each of the segments 520 and 530 may have a shape and size substantially similar to the main segment 510. In other embodiments, the segments 520 and/or 530 may have a shape and/or size different from the main segment 510.

In some embodiments, at least one segment may include an opening. In some embodiments, the guide 500 may include imaging coils disposed within the segment so as to at least partially surround the opening. In some embodiments, the imaging coils may completely surround the opening. By providing the imaging coils around the openings, the underlying anatomy may be better visualized for positioning an instrument mounted on the frame 460.

As shown in the figures, the main segment 510 may include an opening 512. The opening 512 may define a guide region. The guide region may be configured to provide direct visualization of the underlying anatomy and provide a reference for positioning the frame 460 with respect to a target region of the patient. The main segment 510 may include imaging coils 514 encased in the segment 510 and disposed within the segment 510 so to at least partially surround the opening 512.

In some embodiments, all of the segments include openings and include imaging coils that surround the respective opening. As shown in the figures, the segments 520 and 530 may include openings 522 and 532 and imaging coils 524 and 534 encased within the segments 520 and 530, respectively, and disposed within the segments 520 and 530 so as to surround the openings 522 and 532. In some embodiments, the additional segments 520 and/or 530 may have different shaped openings, no openings, different configuration of imaging coils, no imaging coils, or a combination thereof.

In some embodiments, the segments 520 and/or 530 may be flexibly disposed with respect to the segment 510. In some embodiments, the segments 520 and/or 530 may be connected to the segment 510 so that their respective position may be adjustable. In this way, the segments 520 and/or 530 may be configured to be movable with respect to the segment 510. By way of example, positions of the segments 520 and/or 530 can be moved with respect to the segment 510 so as to change the angle between the segments 510 and 520 and/or the angle between the segments 510 and 530, respectively.

In operation, the main segment 510 may be configured to be disposed above the target region of the patient and the additional segments 520 and 530 may be configured to surround sides of the patient. In this way, the guide can more adequately cover the target region. Additionally, the guide can be used in the adjusted based on the position for the patient, for example, supine and/or prone position.

In some embodiments, the system 100 may relate to an assembly of the platform 400 and the imaging guide 500. For example, the platform 400 may be mated with the imaging guide 500, as shown in FIGS. 1-3. In other embodiments, the platform 400 may be mated with a different imaging guide, different system and/or by itself.

In some embodiments, the platform 400 and the imaging guide 500 may include complementary mating members configured to secure the platform 400 to the imaging guide 500. For example, as shown in FIGS. 1-3, 5 and 6, the imaging guide 500 may include a plurality of protruding members 582, 584, 586 and 588 disposed on opposing sides of the main segment 510. The platform 400 may include complimentary openings 482, 484, 486 and 488 disposed on the rail members 410 and 420. In some embodiments, the platform 400 and the imaging guide 500 may include different mating members and/or configuration of mating members. By way of example, the imaging guide 500 (e.g., main segment) can be configured to be mated with the platform 400 so as to be disposed above the platform 400.

In some embodiments, the platform 400 and the imaging guide 500 may be configured to be mated so that at any position, the entry region 462 is within the guide region 512. The platform 400 and the image guide 500 may be disposed so that the procedure region 401 overlaps the guide region 512. In this way, the imaging guide 500 can provide visualization of the anatomy without interfering with the movement of the instrument mounted to the frame 460. Additionally, the imaging guide 500 can provide more accurate position information (e.g., location and orientation) of an instrument mounted to the frame 460 with respect to the target region.

The systems and devices can provide a minimally invasive way to gain access to a target region, for example, disposed on the spine or spinal cord without major surgery. The imaging guide for can provide access to these regions by allowing for visualization of the internal anatomy and targets in the spine/spinal cord during an intraoperative MRI. Therefore, major surgery, such as multi-level laminectomy, to gain access to the spine/spinal cord to provide naked-eye visualization of anatomy to define the target intra-operatively can be avoided. As a result, a procedure using a device and/or system according to embodiments can improve post-operative outcomes, such as reducing the length of the recovery period.

For example, to deliver a therapy to on a target on the spine or spinal cord, the system (e.g., imaging guide and platform) according to embodiments can be mounted to a spine of a patient in a sterile field created in the MRI scanner suite. By way of example, the main segment 510 of the imaging guide 500 may be disposed across the back and/or neck of the patient above the region to be targeted and the other segments 520 and 530 may surround the sides of the patient (e.g., the sides of the back and/or neck). Once the system is attached to the patient and an instrument is mounted to the positioning frame, the patient can be moved in to the gantry of the MR scanner for spine/spinal cord MR imaging and localization of the instrument and the target, from which the planned trajectory may also be determined. The calculated location of the device and the target can allow for a needle/cannula of the instrument to be inserted to the target with the planned trajectory under the guidance of MRI. Once inserted to the target, the location of the needle can be confirmed with MRI and therapeutics can be delivered or a biopsy can be performed. This can allow for high accuracy and intra-operative evidence of successful access to the target. Furthermore, the use of intra-operative MRI can allow for targeting of pathology only visible with MRI, such as MS plaques or SCI lesions. The systems and devices according to embodiments can therefore allow for real-time adjustments and trajectory planning based on intra-operative MRI.

While the disclosure has been described in detail with reference to exemplary embodiments, those skilled in the art will appreciate that various modifications and substitutions may be made thereto without departing from the spirit and scope of the disclosure as set forth in the appended claims. For example, elements and/or features of different exemplary embodiments may be combined with each other and/or substituted for each other within the scope of this disclosure and appended claims.

What is claimed:

1. A guide system, comprising:
an imaging guide including a first segment, the first segment including a guide region and imaging coils surrounding the guide region; and
a platform including:
a first rail having a length;
a second rail having a length, the second rail being disposed parallel to the first rail;
each of the first rail and the second rail including a first track and a second track disposed along the length of the first rail and the second rail, respectively;
the first track and the second track of the first rail being disposed in parallel with respect to the length of the first rail, and the second track of the first rail being disposed below the first track of the first rail;
the first track and the second track of the second rail being disposed in parallel with respect to the length of the second rail, and the second track of the second rail being disposed below the first track of the second rail;
each of the first track of the first rail and the first track of the second rail being disposed at a first height with respect to the first rail and the second rail, respectively;
each of the second track of the first rail and the second track of the second rail being disposed at a second height with respect to the first rail and the second rail, respectively;
a positioning member disposed (i) between the first rail and the second rail and (ii) along the first track of the first rail and the first track of the second rail;
the positioning member being configured to be movable disposed with respect to the first track of the first rail and the first track of the second rail in a first direction;
the positioning member including a first elongated member and a second elongated member that is parallel to the first elongated member;
the positioning member including a positioning frame configured to mount an instrument;
the positioning frame being configured to be movably disposed (i) with respect to the first track of the first rail and the first track of the second rail in the first direction and (ii) with respect to the first elongated member and the second elongated member in a second direction that is perpendicular to the first direction;
the positioning frame having an entry region; and
a first support member and a second support member disposed (i) between the first rail and the second rail and (ii) along the second track of the first rail and the second track of the second rail; and the first support member and the second support member being configured to be movably disposed with respect to the second track of the first rail and the second track of the second rail in the first direction;

wherein the platform is disposed with respect to the imaging guide so that a position of the entry region is within the guide region.

2. The guide system according to claim 1, wherein the platform is fixedly disposed above the first segment.

3. The guide system according to claim 1, wherein:
the platform and the first segment include complementary mating members; and
the platform is configured to mate with the imaging guide so that the platform is above the guide member.

4. The guide system according to claim 1, wherein:
each of the first track and the second track of the first rail and the second rail is a recessed channel disposed within the first rail and the second rail;
each first track has a teethed surface; and
the positioning member includes a member configured to communicate with the teethed surface and move the positioning member along each first track in the first direction.

5. The guide system according to claim 1, wherein:
each of the first support member and the second support member includes one first portion having a length and two second portions disposed on opposite sides of the first portion;
the first portion has a cross-section larger than a cross-section of the two second portions;
the first portion includes a flat surface and an opposing curved surface with respect to its length; and
the first portion includes a plurality of holes disposed along its length extending between the flat surface and the opposing curved surface.

6. The guide system according to claim 1, wherein the imaging guide further includes a second segment and a third segment, the first segment disposed between the second segment and the third segment.

7. The guide system according to claim 6, wherein at least one of the second segment and the third segment are flexibly disposed with respect to the first segment.

8. The guide system according to claim 7, wherein each of the second segment and the third segment includes an opening and imaging coils that surround the opening.

9. The guide system according to claim 1, wherein:
each of the first rail and the second rail includes a first end, a second end, and a length therebetween;
the platform further includes a first member fixedly disposed to the first end of the first rail and the first end of the second rail and a second member fixedly disposed to the second end of the first rail and the second end of the second rail;
the first member and the second member is parallel to the first support member and the second support member;
the first support member and the second support member is disposed along the first rail and the second rail to be parallel to the positioning member, the first support member and the second support member being configured to linearly move along the second track of the first rail and the second track of the second rail and rotate with respect to the first and second rails;
the positioning member being disposed between the first support member and the second support member with respect to the first rail and the second rail; and the first support member, the second support member, the first rail, and the second rail define a procedure region in which the positioning member is positioned.

10. The guide system according to claim 9, wherein:
the platform overlaps the imaging guide so that the procedure region at least partially overlaps the guide region.

11. A guide system, comprising:
an imaging guide including a first segment, the first segment including a guide region and imaging coils surrounding the guide region;
a platform including:
a first rail having a length;
a second rail having a length, the second rail being disposed parallel to the first rail;
each of the first rail and the second rail including a first track and a second track disposed along the length of the first rail and the second rail, respectively;
the first track and the second track of the first rail being disposed in parallel with respect to the length of the first rail, and the second track of the first rail being below the first track of the first rail;
the first track and the second track of the second rail being disposed in parallel with respect to the length of the second rail, and the second track of the first rail being below the first track of the first rail;
each of the first track of the first rail and the first track of the second rail being disposed at a first height with respect to the first rail and the second rail, respectively;
each of the second track of the first rail and the second track of the second rail being disposed at a second height with respect to the first rail and the second rail, respectively;
a positioning member disposed (i) between the first rail and the second rail and (ii) along the first track of the first rail and the first track of the second rail;
the positioning member being configured to be movable disposed with respect to the first track of the first rail and the first track of the second rail in a first direction;
the positioning member including a first elongated member and a second elongated member that is parallel to the first elongated member;
the positioning member including a positioning frame configured to mount an instrument;
the positioning frame being configured to be movably disposed (i) with respect to the first track of the first rail and the first track of the second rail in the first direction and (ii) with respect to the first elongated member and the second elongated member in a second direction that is perpendicular to the first direction;
the positioning frame having an entry region; and
a first support member and a second support member disposed (i) between the first rail and the second rail and (ii) along the second track of the first rail and the second track of the second rail;
the first support member and the second support member being configured to be movably disposed with respect to the second track of the first rail and the second track of the second rail in the first direction; and
the first support member, the second support member, the first rail, and the second rail define a procedure region in which the positioning member is positioned;

wherein the imaging guide is configured to mate with the platform so that the procedure region at least partially overlaps the imaging guide.

12. The guide system according to claim 11, wherein the imaging coils are radiofrequency coils encased in the first segment.

13. The guide system according to claim 11, wherein:
each of the first support member and the second support member includes one first portion having a length and two second portions disposed on opposite sides of the first portion;
the first portion has a cross-section larger than a cross-section of the two second portions;
the first portion includes a flat surface and an opposing curved surface with respect to its length; and
the first portion includes a plurality of holes disposed along its length extending between the flat surface and the opposing curved surface.

14. The guide system according to claim 11, wherein the positioning member is disposed between the first support member and the second support member with respect to the first rail and the second rail.

15. The guide system according to claim 11, further comprising:
a second segment and a third segment, the first segment disposed between the second segment and the third segment.

16. The guide system according to claim 15, wherein:
at least one of the second segment or third segment are flexibly disposed with respect to the first segment; and
at least one of the second segment or third segment are configured to be adjusted with respected to the first segment so that at least one of an angle between the first segment and the second segment or an angle between the first segment and the third segment is adjusted.

17. A guide system, comprising:
a surgical platform, the surgical platform including:
a first rail having a length;
a second rail having a length, the second rail being disposed parallel to the first rail;
each of the first rail and the second rail including a first track and a second track disposed along the length of the first rail and the second rail, respectively;
the first track and the second track of the first rail being disposed in parallel with respect to the length of the first rail, and the second track of the first rail being disposed below the first track of the first rail;
the first track and the second track of the second rail being disposed in parallel with respect to the length of the second rail, and the second track of the second rail being disposed below the first track of the second rail;
each of the first track of the first rail and the first track of the second rail being disposed at a first height with respect to the first rail and the second rail, respectively;
each of the second track of the first rail and the second track of the second rail being disposed at a second height with respect to the first rail and the second rail, respectively;
a positioning member disposed (i) between the first rail and the second rail and (ii) along the first track of the first rail and the first track of the second rail;
the positioning member being configured to be movable disposed with respect to the first track of the first rail and the first track of the second rail in a first direction;
the positioning member including a first elongated member and a second elongated member that is parallel to the first elongated member;
the positioning member including a positioning frame configured to mount an instrument;
the positioning frame being configured to be movably disposed (i) with respect to the first track of the first rail and the first track of the second rail in the first direction and (ii) with respect to the first elongated member and the second elongated member in a second direction that is perpendicular to the first direction;
the positioning frame having an entry region; and
a first support member and a second support member disposed (i) between the first rail and the second rail and (ii) along the second track of the first rail and the second track of the second rail; and
the first support member and the second support member being configured to be movably disposed with respect to the second track of the first rail and the second track of the second rail in the first direction.

18. The guide system according to claim 17, wherein the platform is configured to mate with an imaging guide including imaging coils.

19. The guide system according to claim 18, further comprising:
wherein the imaging guide includes a first segment, the first segment including a guide region and imaging coils surrounding the guide region; and
wherein the platform is disposed with respect to the imaging guide so that a position of the entry region is within the guide region.

* * * * *